US009012168B2

(12) United States Patent
Ruiz et al.

(10) Patent No.: US 9,012,168 B2
(45) Date of Patent: Apr. 21, 2015

(54) ASSAYS FOR DETECTION OF GLYCOSAMINOGLYCANS

(75) Inventors: Juan Ruiz, Acton, MA (US); Marcia Sellos-Moura, West Newbury, MA (US); Philip Shi, Newton, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 4 days.

(21) Appl. No.: 13/813,113

(22) PCT Filed: Jul. 29, 2011

(86) PCT No.: PCT/US2011/046018
§ 371 (c)(1), (2), (4) Date: Apr. 11, 2013

(87) PCT Pub. No.: WO2012/016216
PCT Pub. Date: Feb. 2, 2012

(65) Prior Publication Data
US 2013/0189718 A1    Jul. 25, 2013

Related U.S. Application Data

(60) Provisional application No. 61/369,022, filed on Jul. 29, 2010.

(51) Int. Cl.
*C12Q 1/37*     (2006.01)
*G01N 21/75*    (2006.01)
*G01N 33/68*    (2006.01)

(52) U.S. Cl.
CPC ........ *G01N 21/75* (2013.01); *C12Q 1/37* (2013.01); *G01N 33/6893* (2013.01); *G01N 2400/40* (2013.01); *G01N 2500/00* (2013.01); *G01N 2800/042* (2013.01); *G01N 2800/52* (2013.01)

(58) Field of Classification Search
USPC ........................................................ 435/23
See application file for complete search history.

(56) References Cited

U.S. PATENT DOCUMENTS

| | | | |
|---|---|---|---|
| 5,310,646 A | 5/1994 | Whitley | |
| 5,646,007 A | 7/1997 | Enomoto et al. | |
| 5,985,582 A | 11/1999 | Triscott | |
| 7,005,271 B1 | 2/2006 | Freyssinet et al. | |
| 7,083,937 B2 | 8/2006 | Sadisekharan | |
| 2003/0124705 A1 | 7/2003 | Berry et al. | |
| 2005/0238536 A1 | 10/2005 | Striepeke et al. | |
| 2006/0259987 A1 | 11/2006 | Bock et al. | |
| 2007/0042993 A1 | 2/2007 | Manoni et al. | |
| 2009/0087870 A1 | 4/2009 | Calatzis et al. | |
| 2009/0092996 A1 | 4/2009 | Clarke et al. | |
| 2009/0280505 A1 | 11/2009 | Okamura et al. | |
| 2009/0298103 A1 | 12/2009 | Mann et al. | |
| 2010/0137194 A1 | 6/2010 | Lawrence et al. | |
| 2011/0281820 A1 | 11/2011 | Oreste et al. | |
| 2012/0009616 A1 | 1/2012 | Crawford et al. | |

FOREIGN PATENT DOCUMENTS

WO    WO-2010078511 A2    7/2010

OTHER PUBLICATIONS

Bourin, et al., "Glycosaminoglycans and the regulation of blood coagulation" Biochem. J. 289: 313-330 (1993).
Cooper et al., "The phenotypic and genetic assessment of antithrombin deficiency", Int. Jnl Lab Hem. 33: 227-237 (2011).
Guerrini, et al., "Antithrombin-binding Octasaccharides and Role of Extensions of the Active Pentasaccharide Sequence in the Specificity and Strength of Interaction", The Journal of Biological Chemistry 283(39): 26662-26675 (2008).
Hurst, et al, "Structure-Activity Relationships of Heparin—Independence of Heparin Charge Density and Antithrombin-Binding Domains in Thrombin Inhibition by Antithrombin and Heparin Cofactor II", J. Clin Invest 72: 1042-1045 (1983).
Mushunje, et al., "Heparin-induced substrate behavior of antithrombin Cambridge II", Blood 102(12): 4028-4034 (2003).
Olson, et al., "Predominant Contribution of Surface Approximation to the Mechanism of Heparin Acceleration of the Antithrombin-Thrombin Reaction", The Journal of Biological Chemistry 266(10): 6353-6364 (1991).
Tomatsu, et al., "Dermatan sulfate and heparan sulfate as a biomarker for mucopolysaccharidosis I", J. Inferit Metab Dis 33:141-150 (2010).
Tollefsen, at al., "Activation of Heparin Cofactor II by Dermatan Sulfate", The Journal of Biochemistry 258(11): 6713-6716 (1983).
Liu, et al. "A heparin-binding synthetic peptide of heparin/heparan sulfate-interacting protein modulates blood coagulation activities". Proc. Nail, Acad. Sci. USA. 94: 1739-1744 (1997).
Senzolo, et al. "The effects of glycosaminoglycans on coagulation: a thromboelastographic study". Blood Coagulation Fibrinolysis. 18(3): 227-36. (2007).
Lee, et al., "Dermatan Sulfate Proteoglycan and Glycosaminoglycan Synthisis is Induced in Fibroblasts by Transfer to a Three-dimensional Extracellular Environment". J Biol Chern. 279(47): 48640-48646 (2004).
Dol et al., "Pharmacodynamics and pharmacokinetics of dermatan sulfate in humans". Blood. 74(5):1577-82. (1989).
Chromogenix, COATEST Herapin, Product Information 2001, Art. No. 25 55 39, [online]. [Retrieved on Nov. 22, 2011]. Retrieved from the Internet: <URL: http://heparinmonitoring.com/downloads/Insert%20-%20Coatest%20Heparin.pdf>Entire documentation, especially Measurment principle.
Shrader, et al. "Neutral inhibitors of the serine protease factor Xa". Bioorganic & Medicinal Chemistry Letter 11(14):1801-1804 (2001).
Michel, et al., "The Structure of Chondroitin B Lyase Complexed with Glycosamingoglycan Oligosaccharides Unravels a Calcium-dependent Ctalytic Machinery". J. Biol Chem 279(31): 32882-32896 (2004).

(Continued)

*Primary Examiner* — Maryam Monshipouri
(74) *Attorney, Agent, or Firm* — Choate, Hall & Stewart LLP; Fangli Chen; Rolando Medina

(57) ABSTRACT

Disclosed herein are novel methods, assays and kits useful for the diagnosis and monitoring of subjects with mucopolysaccharidoses (MPS), The methods, assays and kits are particularly useful for detecting the presence of one or more glycosaminoglycans which correlate to MPS and its severity in a variety of biological samples.

13 Claims, 8 Drawing Sheets

(56) References Cited

OTHER PUBLICATIONS

Wikipedia_Heparin, Last modified: Nov. 17, 2011 [online]. [Retrieved on Nov. 22, 2011]. Retrieved from the Internet: <URL: http://en.wikipedia.org/wiki/Heparin>. Entire documentation.

International Search Report for International Application PCT/US2011/046018, dated Feb. 27, 2012.

Abildgaard et al., Assay of Dermatan Sulfate Cofactor (Heparin Cofactor II) Activity in Human Plasma, Thrombosis Research, 35(3):257-266 (1984).

Langford-Smith et al., Evaluation of Heparin Cofactor II Thrombin Complex as a Biomarker on Blood Spots from Mucopolysaccharidosis I, IIIA and IIIB mice, Molecular Genetics and Metabolism, 99(3):269-274 (2010).

Abildgaard et al., Antithrombin (Heparin Cofactor) Assay with "New" Chromogenic Substrates (S-2238 and Chromozym TH), Thrombosis Research, 11(4):549-553 (1977).

Dickson, et al. "Intrathecal enzyme replacement therapy: Successful treatment of brain disease via the cerebrospinal fluid". Molecular Genetics and Metabolism 91: 61-68 (2007).

Hitchcock, et al, "Glycoform Quantification of Chondroitin/Dermatan Sulfate Using a Liquid Chromatography—Tandem Mass Spectrometry Platform", Biochemistry 45: 2350-2361 (2006).

Oguma, et al, "Analytical method for the determination of disaccharides derived from keratan, heparan, and dermatan sulfates in human serum and plasma by high-performance liquid chromatography/turbo ionspray ionization tandem mass spectrometry". Analytical Biochemistry 368:79-86 (2007).

Randall, et al., "Heparin cofactor II-thrombin complex: A biomarker of MPS disease". Molecular Genetics and Metabolism, 94: 456-461 (2008).

Metcalf, et al., "Mechanism of Shortened Bones in Mucopolysaccharidosis VII", Mol. Genet. Metab 97(3): 202-211 (2009).

International Search Report for International Application PCT/US2013/24379, dated Jun. 19, 2013.

DS Calibration Curve in Buffer (ng/ml)

| Sample | Concentration | Wells | Values | MeanValue | Std Dev | CV% | BackCalc |
|---|---|---|---|---|---|---|---|
| sta01 | 40.000 | A1 | 0.122 | 0.125 | 0.003 | 2.6 | 37.56 |
|  |  | A2 | 0.125 |  |  |  |  |
|  |  | A3 | 0.128 |  |  |  |  |
| sta02 | 30.000 | B1 | 0.175 | 0.178 | 0.003 | 1.5 | 20.43 |
|  |  | B2 | 0.180 |  |  |  |  |
|  |  | B3 | 0.179 |  |  |  |  |
| sta03 | 20.000 | C1 | 0.346 | 0.356 | 0.010 | 2.7 | 20.51 |
|  |  | C2 | 0.358 |  |  |  |  |
|  |  | C3 | 0.365 |  |  |  |  |
| sta04 | 15.000 | D1 | 0.638 | 0.670 | 0.034 | 5.1 | 15.06 |
|  |  | D2 | 0.672 |  |  |  |  |
|  |  | D3 | 0.703 |  |  |  |  |
| sta05 | 10.000 | E1 | 1.282 | 1.327 | 0.042 | 3.1 | 9.87 |
|  |  | E2 | 1.334 |  |  |  |  |
|  |  | E3 | 1.364 |  |  |  |  |
| sta06 | 5.000 | F1 | 2.063 | 2.049 | 0.051 | 2.5 | 5.25 |
|  |  | F2 | 2.091 |  |  |  |  |
|  |  | F3 | 1.993 |  |  |  |  |
| sta07 | 2.500 | G1 | 2.273 | 2.247 | 0.039 | 1.8 | 2.47 |
|  |  | G2 | 2.267 |  |  |  |  |
|  |  | G3 | 2.202 |  |  |  |  |
| sta08 | 0.000 | H1 | 2.308 | 2.288 | 0.028 | 1.2 | Range? |
|  |  | H2 | 2.301 |  |  |  |  |
|  |  | H3 | 2.256 |  |  |  |  |

Smallest standard value: 0.125
Largest standard value: 2.288

FIG. 2

HS Calibration Curve in Buffer (ng/ml)

| Sample | Wells | Conc ng/ml | Values | MeanValue | CV val | BackCalc |
|---|---|---|---|---|---|---|
| St01 | A11 | 20 | 0.190 | 0.187 | 1.8 | 17.833 |
| | A12 | | 0.185 | | | 18.206 |
| St02 | B11 | 10 | 0.387 | 0.357 | 12.0 | 10.848 |
| | B12 | | 0.327 | | | 12.102 |
| St03 | C11 | 15 | 0.260 | 0.254 | 3.1 | 14.107 |
| | C12 | | 0.248 | | | 14.546 |
| St04 | D11 | 8 | 0.704 | 0.724 | 4.0 | 7.361 |
| | D12 | | 0.745 | | | 7.079 |
| St05 | E11 | 5 | 1.114 | 1.167 | 6.4 | 5.144 |
| | E12 | | 1.219 | | | 4.709 |
| St06 | F11 | 3 | 1.763 | 1.798 | 2.8 | 2.691 |
| | F12 | | 1.833 | | | 2.407 |
| St07 | G11 | 1 | 1.960 | 2.010 | 3.5 | 1.809 |
| | G12 | | 2.060 | | | 1.131 |
| St08 | H11 | 0 | 2.130 | 2.149 | 1.3 | Range? |
| | H12 | | 2.168 | | | Range? |

FIG. 4

HS Curve in 5% CSF (ng/ml)

| Sample | Concentration | Wells | Values | MeanValue | Std.Dev | CV% | BackCalc |
|---|---|---|---|---|---|---|---|
| sta01 | 20.000 | A1 | 0.167 | 0.173 | 0.007 | 3.8 | 19.21 |
| | | A2 | 0.173 | | | | |
| | | A3 | 0.180 | | | | |
| sta02 | 15.000 | B1 | 0.232 | 0.245 | 0.015 | 6.0 | 15.21 |
| | | B2 | 0.243 | | | | |
| | | B3 | 0.261 | | | | |
| sta03 | 10.000 | C1 | 0.435 | 0.450 | 0.014 | 3.2 | 10.13 |
| | | C2 | 0.453 | | | | |
| | | C3 | 0.464 | | | | |
| sta04 | 7.500 | D1 | 0.669 | 0.682 | 0.019 | 2.9 | 7.51 |
| | | D2 | 0.672 | | | | |
| | | D3 | 0.704 | | | | |
| sta05 | 5.000 | E1 | 1.048 | 1.094 | 0.040 | 3.7 | 4.98 |
| | | E2 | 1.113 | | | | |
| | | E3 | 1.122 | | | | |
| sta06 | 2.500 | F1 | 1.773 | 1.789 | 0.017 | 0.9 | 2.46 |
| | | F2 | 1.807 | | | | |
| | | F3 | 1.788 | | | | |
| sta07 | 1.250 | G1 | 2.142 | 2.119 | 0.021 | 1.0 | 1.34 |
| | | G2 | 2.113 | | | | |
| | | G3 | 2.101 | | | | |
| sta08 | 0.000 | H1 | 2.361 | 2.326 | 0.038 | 1.6 | Range? |
| | | H2 | 2.332 | | | | |
| | | H3 | 2.286 | | | | |

Smallest standard value: 0.173
Largest standard value: 2.326

FIG. 6

ASSAYS FOR DETECTION OF GLYCOSAMINOGLYCANS

RELATED APPLICATIONS

This application is a national stage filing under stage filing under 35 U.S.C. 371 of International Application PCT/US2011/046018, filed Jul. 29, 2011, which claims the benefit of U.S. Provisional Application Ser. No. 61/369,022, filed on Jul. 29, 2010, the entire teachings of which are incorporated herein by reference. International Application PCT/US2011/046018 was published under PCT Article 21(2) in English.

BACKGROUND OF THE INVENTION

The mucopolysaccharidoses (MPS) represent a group of rare, inherited lysosomal storage disorders caused by the deficiency or inactivity of lysosomal enzymes. In particular, the MPS disorders are caused by the deficiency or inactivity of the lysosomal enzymes which catalyze the stepwise metabolism of complex sugar molecules known as glycosaminoglycans (GAGs). These enzyme deficiencies in turn result in the accumulation of GAGs in the cells, tissues, and, in particular, cellular lysosomes of affected subjects, resulting in permanent, progressive cellular damage which affects appearance, physical abilities, organ and system functioning, and, in most cases, mental development of affected subjects.

Eleven discrete enzyme deficiencies have been identified, which result in seven distinct clinical classes of MPS. Each MPS disorder is characterized by a deficiency or inactivity of an enzyme involved in the metabolism of one or more of the GAGS heparan sulfate (HS), dermatan sulfate (DS), chondroitin sulfate (CS), keratan sulfate (KS) or hyaluronan. As a result, such GAGs accumulate in the cells and tissues of affected subjects.

The diagnosis of MPS and the monitoring of both disease progression and treatment efficacy rely on subjective and objective monitoring of the subject. Available objective assays useful for the diagnosis of MPS and for monitoring treatment efficacy have traditionally lacked sensitivity, have significant limitations, and have been characterized as inadequate (see for example, Oguma T, et al., Analytical Biochemistry (2007) 368: 79-86.)

Diagnosis of MPS can be made through urinalysis. For example, the use of diagnostic methods which rely on spectrophotometry to measure total GAGs in urine are based upon binding to dimethylmethylene blue, and are limited to use in urinary assays. Furthermore, the utility of urinalysis determinations, may not be indicative of a specific MPS disorder because the presence of excess GAGs in the urine of a subject may only provide objective evidence that either one of the several MPS disorders are present. (Neufeld E F, et al., The mucopolysaccharidoses. In: Scriver CR, ed. The Metabolic and Molecular Bases of Inherited Disease. New York, N.Y.: McGraw-Hill (2001) 3421-3452.) Similarly, urinalysis assays which analyze GAGs content in the urine are not particularly sensitive and a negative urine GAGs test may not necessarily preclude a diagnosis of MPS. Reported assays based on the use of enzymatic digestion of GAGs and high-performance liquid chromatography (HPLC) detection of the corresponding disaccharides are also limited, for example due to their lack of specificity and/or sensitivity.

Reported assays which measure biological markers correlating to MPS also have limitations. For example, assays which measure serum levels of a heparin cofactor-II-thrombin complex (THC) have been described as a monitoring tool for subjects with MPS. (Randall, D R, et al. Molecular Genetics and Metabolism (2008), 94: 456-461.) Such assays however, are of limited use in MPS classes where the accumulating pathological GAG is not primarily dermatan sulfate, such as in MPS-III, MPS-IV, MPS-VII or MPS-IX, since under physiological conditions formation of THC is not efficiently catalyzed by HS, CS, KS or hyaluronan.

New screening methods, assays and biological markers are needed to diagnosis MPS and to monitor clinical course and disease progression/regression before, during and after treatment. In particular new assays that are useful for quantifying GAGs in a variety of biological samples (e.g., serum, urine, and CSF) would be useful to monitor disease severity, progression and treatment efficacy.

SUMMARY OF THE INVENTION

The present invention relates to novel methods, assays and kits useful for identifying subjects having mucopolysaccharidoses (MPS), as well as to monitor disease severity, progression and treatment efficacy. The methods, assays and kits of the present invention are particularly useful for detecting the presence or absence of one or more glycosaminoglycans (e.g., dermatan sulfate and heparan sulfate) in a variety of biological samples (e.g., serum, urine, and CSF) and provide a means of diagnosing MPS, determining MPS severity, or alternatively for determining the responsiveness of MPS to therapeutic agents and regimens administered to a subject for the treatment of MPS.

As described herein, assays are disclosed which combine a serine protease, an inhibitor of the serine protease, and a substrate for the serine protease, along with one or more glycosaminoglycans (e.g., in a sample), under conditions suitable for cleavage of the serine protease substrate by the serine protease. Presence of the serine protease inhibitor inhibits the activity of the serine protease on its substrate, and presence of the one or more glycosaminoglycans improves, catalyzes or facilitates this inhibition. As a result, cleavage of the serine protease substrate is inhibited to a greater extent in the presence of one or more glycosaminoglycans than in the absence of glycosaminoglycans. Substrates suitable for use in the assays will typically be chromogenic or fluorogenic substrates whose cleavage products are detectable by spectrophotometric means. After the components of the assay are combined for a suitable time period, spectrophotometric analysis is performed, and the results are compared against a standard which calibrates absorbance with glycosaminoglycan concentration. In this way the concentration of glycosaminoglycan in the sample can be determined.

In certain embodiments, the methods and assays of the present invention may comprise a step of determining the quantity and/or concentration of one or more glycosaminoglycans in a biological sample by comparatively assessing the concentration of such glycosaminoglycans (e.g., using spectroscopy) relative to one or more standard or calibration curves which have been constructed using standard solutions with known quantities of such glycosaminoglycans. Alternatively, the methods and assays of the present invention may be used to determine the concentration of one or more GAGs by comparison to one or more controls.

Also contemplated are kits for determining the concentration and/or quantity of one or more glycosaminoglycans. Such kits preferably include one or more reagents (e.g., one or more of a serine protease, a labeled substrate for said serine protease, an inhibitor of said serine protease, standards, buffers, instructions for carrying out a method in accordance with the present invention, and combinations thereof).

Disclosed is a method for determining the concentration of one or more glycosaminoglycans in a sample comprising (a) combining a serine protease (e.g., of the clotting cascade), a labeled substrate for said serine protease, an inhibitor of said serine protease, and a sample suspected of comprising one or more glycosaminoglycans under conditions and for a time suitable for cleavage of the labeled substrate by the serine protease to produce a detectable signal, (b) detecting the detectable signal, and (c) comparing the amount of detectable signal with a standard to determine the concentration of said one or more glycosaminoglycans in said sample, wherein said inhibitor of said serine protease is selected from the group consisting of heparin cofactor II and antithrombin III, and wherein said one or more glycosaminoglycans are selected from the group consisting of dermatan sulfate (DS) and heparin sulfate (HS).

Also disclosed is a method of identifying an individual having a mucopolysaccharidosis (MPS), comprising determining the concentration of one or more glycosaminoglycans in a biological sample obtained from said individual by a method comprising (a) combining a serine protease (e.g., of the clotting cascade), a labeled substrate for said serine protease, an inhibitor of said serine protease, and a biological sample from said subject under conditions and for a time suitable for cleavage of the labeled substrate by the serine protease to produce a detectable signal, (b) detecting the detectable signal, and (c) comparing the amount of detectable signal with a standard to determine the concentration of said one or more glycosaminoglycans in said sample, wherein said inhibitor of said serine protease is selected from the group consisting of heparin cofactor II and antithrombin III, wherein said one or more glycosaminoglycans are selected from the group consisting of dermatan sulfate (DS) and heparan sulfate (HS), and wherein the concentration of said one or more glycosaminoglycans is indicative of whether the individual has MPS.

Also disclosed is a method of determining the efficacy of one or more therapeutic agents or regimens for treatment of mucopolysaccharidosis (MPS) comprising determining the concentration of one or more glycosaminoglycans in a first biological sample obtained from an individual prior to administration of one or more therapeutic agents or regimens to said individual, determining the concentration of said glycosaminoglycans in a second biological sample obtained from said individual after administration of one or more therapeutic agents or regimens to said individual, wherein if the concentration of said glycosaminoglycans in said second biological sample is lower than the concentration in said first biological sample the one or more therapeutic agents or regimens are efficacious for treatment of MPS, and wherein determining the concentration of one or more glycosaminoglycans in the first and second biological samples is performed by a method comprising (a) combining a serine protease (e.g., of the clotting cascade), a labeled substrate for said serine protease, an inhibitor of said serine protease, and the first or second biological sample under conditions and for a time suitable for cleavage of the labeled substrate by the serine protease to produce a detectable signal, (b) detecting the detectable signal, and (c) comparing the amount of detectable signal with a standard to determine the concentration of said one or more glycosaminoglycans in said sample, wherein said inhibitor of said serine protease is selected from the group consisting of heparin cofactor II and antithrombin III, and wherein said one or more glycosaminoglycans are selected from the group consisting of dermatan sulfate (DS) and heparin sulfate (HS).

Also disclosed is a method of determining the progression of a mucopolysaccharidosis (MPS) disorder in an individual, comprising determining the concentration of one or more glycosaminoglycans in a first biological sample obtained from an individual and determining the concentration of said one or more glycosaminoglycans in one or more subsequent biological samples obtained from said individual, wherein if the concentration of said one or more glycosaminoglycans in said one or more subsequent biological samples is greater than the concentration in said first biological sample it is indicative that the MPS is progressing, and wherein determining the concentration of one or more glycosaminoglycans in the first and subsequent biological samples is performed by a method comprising (a) combining a serine protease, a labeled substrate for said serine protease, an inhibitor of said serine protease, and the first or subsequent biological sample under conditions and for a time suitable for cleavage of the labeled substrate by the serine protease to produce a detectable signal, (b) detecting the detectable signal, and (c) comparing the amount of detectable signal with a standard to determine the concentration of said one or more glycosaminoglycans in said sample, wherein the serine protease is a serine protease of the clotting cascade, wherein said inhibitor of said serine protease is selected from the group consisting of heparin cofactor II and antithrombin III, and wherein said one or more glycosaminoglycans are selected from the group consisting of dermatan sulfate (DS) and heparan sulfate (HS).

In some embodiments the serine protease is selected from the group consisting of the serine proteases shown in FIG. 7 and FIG. 8.

In some embodiments the labeled substrate is a chromogenic or fluorogenic substrate.

In some embodiments the serine protease is thrombin and the labeled substrate is a chromogenic thrombin substrate.

In some embodiments the sample is treated to inactivate all but one of the glycosaminoglycans in the sample. In some embodiments the sample is treated with chondroitinase B and the active glycosaminoglycan is dermatan sulfate. In some embodiments the sample is treated with heparinases and the active glycosaminoglycan is heparan sulfate.

In some embodiments detecting the detectable signal is performed by spectrophotometric detection. In some embodiments the spectrophotometric detection is performed at 405 nm.

In some aspects the sample is a biological sample. In some aspects the sample is selected from the group consisting of urine, serum, cerebrospinal fluid, and saliva.

In some embodiments the standard is a curve which calibrates spectrophotometric absorbance with glycosaminoglycan concentration.

In some aspects the MPS is selected from the group consisting of MPS I, MPS II, MPS IIIA, MPS IIIB, MPS IIIC, MPS IIID, MPS IVA, MPS IVB, MPS VI, MPS VII and MPS IX.

In some aspects the one or more therapeutic agents or regimens are selected from the group consisting of enzyme replacement therapies, bone marrow transplantation, and combinations thereof. In some embodiments the one or more therapeutic agents are selected from the group consisting of iduronate sulfatase, idursulfase, alpha-L-iduronidase, heparin sulfamidase, N-acetylglucosaminidase, N-acetylglucosamine 6-sulfatase, N-acetylgalactosamine-4-sulfatase and beta-glucoronidase.

BRIEF DESCRIPTION OF THE DRAWINGS

FIG. 2 illustrates sample Dermatan Sulfate (DS) Calibrator absorbance values in Assay Buffer 1.

FIG. 4 illustrates sample Heparan Sulfate (HS) Calibrator absorbance values in Assay Buffer 2.

FIG. 6 illustrates sample Heparan Sulfate (HS) Calibrator absorbance values in 5% cerebrospinal fluid (CSF) in Assay Buffer 2.

DETAILED DESCRIPTION OF THE INVENTION

Figure 1:
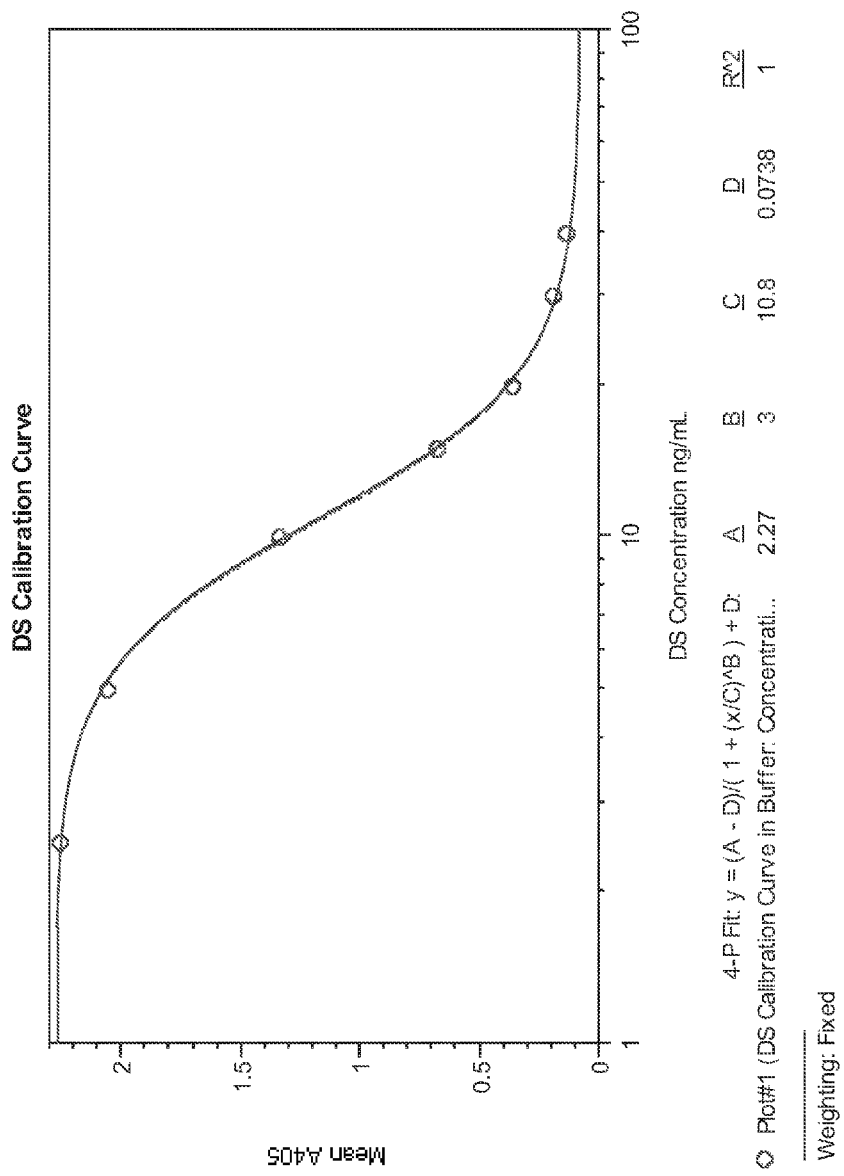
FIG. 1 illustrates sample Dermatan Sulfate (DS) Standard Curve in Assay Buffer 1.

The present invention is based on the discovery that under optimized conditions glycosaminoglycans (e.g., dermatan sulfate and heparan sulfate) may be indirectly measured in a biological sample, and provide a means of diagnosing MPS and/or monitoring disease progression or the efficacy of a therapeutic agent and/or regimen administered to a subject with MPS. Specifically, the present invention relates to novel methods, assays and kits useful for identifying subjects having MPS and for measuring or monitoring response to therapy and disease progression. The methods, assays and kits of the present invention are particularly useful for indirectly detecting the presence of and/or quantifying one or more glycosaminoglycans in a variety of biological samples (e.g., serum, urine, and CSF) and thus provide a means of diagnosing MPS, determining MPS severity, or alternatively for determining the responsiveness of MPS to therapeutic agents administered for the treatment of MPS.

The MPS disorders are lysosomal storage diseases, characterized by malfunctioning lysosomes. As used herein, the terms "mucopolysaccharidoses" or "MPS" mean any of a group of genetic disorders involving a defect in the metabolism of glycosaminoglycans resulting in greater than normal levels of such glycosaminoglycans in the cells and tissues of a subject. Examples of MPS disorders and the corresponding deficient enzymes and accumulated GAGs are shown below in Table 1.

TABLE 1

MPS Disorders

| TYPE | DISEASE | DEFICIENT ENZYME | ACCUMULATED GAGs |
|---|---|---|---|
| MPS-I | Hurler syndrome | α-L-iduronidase | HS, DS |
| MPS-II | Hunter syndrome | Iduronate 2-sulfatase | HS, DS |
| MPS-IIIA | Sanfilippo syndrome A | Heparan sulfate N-sulfatase | HS |
| MPS-IIIB | Sanfilippo syndrome B | N-acetyl-α-D-glucosaminidase | HS |
| MPS-IIIC | Sanfilippo syndrome C | acetyl-CoA-α-glucosaminide N-acetyltransferase | HS |
| MPS-IIID | Sanfilippo syndrome D | N-acetylgucosamine-6-sulfatase | HS |
| MPS-IVA | Morquio syndrome A | N-acetylgalactosamine-6-sulfatase | KS, CS |
| MPS-IVB | Morquio syndrome B | β-galaetosidase | KS |
| MPS-VI | Maroteaux-Lamy syndrome | N-acetylgalactosamine-4-sulfatase | DS |
| MPS-VII | Sly syndrome | β-glucuronidase | HS, DS, CS |
| MPS-IX | Natowicz syndrome | Hyaluronidase | Hyaluronic acid |

Subjects with MPS either do not produce enough of one of the 11 enzymes required to metabolize GAGs into degradation products and simpler disaccharide molecules, or produce enzymes that do not function properly. Over time, the GAGs accumulate in the cells, blood, and connective tissues, resulting in permanent, progressive cellular damage that affects the subject's appearance, physical abilities, organ and system functioning, and, frequently, mental development.

There is currently no cure for MPS, and treatment options are limited. Palliative care may be offered to subjects to improve their quality of life. Additionally, bone marrow transplantation may be considered a viable therapeutic option for some subjects with MPS, although the availability and efficacy of bone marrow transplant is frequently limited to subjects who are strong enough to endure the procedure.

Enzyme replacement therapy (ERT) has been shown to be a useful therapeutic alternative for some MPS subjects. For example, clinical studies have demonstrated that administration of recombinant alpha-L-iduronidase can alter the phenotype of MPS I patients to varying degrees (Wraith, J E, et al., J. Pediatr. (2004) 144: 581-588). The phrase "therapeutic agent" as used herein, refers to any treatment anticipated to affect (i.e., improve or slow progression) MPS disease progression (e.g., as objectively measured using the methods, assays and kits described herein), and include, without limitation ERT (e.g., alpha-L-iduronidase, iduronate 2-sulfatase (such as idursulfase), heparin sulfamidase, N-acetylglucosaminidase, N-acetylglucosamine 6-sulfatase, N-acetylgalactosamine-4-sulfatase and beta-glucoronidase) and bone marrow transplants. In accordance with one embodiment of the present invention, the kits, assays and methods of the present invention may be used to monitor disease progression or the efficacy of a therapeutic agent administered to a subject.

The methods, assays and kits of the present invention may advantageously be employed using various biological samples. As the phrase is used herein, "biological sample" means any sample taken or derived from a subject. Examples of contemplated biological samples include cerebrospinal fluid, tissues such as chorionic villus, cell samples, organs, biopsies, blood, serum, amniotic fluid, saliva and urine. In some embodiments the biological sample will contain additional proteins. Also contemplated by the present invention is a differential analysis of more than one biological sample obtained from a subject (e.g., two, three, four, five, six or more biological samples), for example to monitor disease progression, regression or treatment efficacy. Such samples may be distinguished herein by reference to a first biological sample and a second (or subsequent) biological sample. In a preferred embodiment, such first biological sample and such second biological samples are obtained from a subject at varying intervals (e.g., before and after the administration of a therapeutic agent or initiation of MPS therapy). Similarly, biological samples may be at multiple time points, e.g., collected over the course of a subject's lifetime, to monitor disease progression, and comparative analyses of such samples may be used to inform treatment decisions (e.g., increasing or decreasing the dose of a therapeutic agent, or discontinuing a therapeutic agent in favor of initiating another therapeutic agent or regimen). The skilled artisan will be able to make MPS diagnostic, prognostic, and progressive determinations based on art-recognized correlations between GAG concentrations/amounts and MPS status, optionally in combination with other diagnostic and prognostic indicators.

The methods, assays and kits of the present invention advantageously provide a means of measuring MPS disease progression, e.g., in the central nervous system (CNS), by assaying cerebrospinal fluid (CSF). The ability to assay CSF is particularly useful for the monitoring of subjects with MPS disorders that are characterized as having a CNS etiology, such as Sanfilippo syndrome and Hunter syndrome.

In the context of the present invention, the term "subject" refers to a mammal, and the term "individual" refers to a human. Contemplated subjects and individuals include those suspected of having an MPS disorder and those with a confirmed MPS disorder.

The methods and assays of the present invention are directed to measuring the accumulated glycosaminoglycans as a means of either diagnosing MPS or monitoring disease progression or treatment efficacy. The terms "glycosaminoglycan" or "GAGs" refer to sulfated heteropolysaccharide molecules of varying lengths containing repeating disaccharide units. In some embodiments of the present invention, the GAGs are exemplified by heparan sulfate (HS), dermatan sulfate (DS), chondroitin sulfate, keratan sulfate or hyaluronan.

Specifically, the assays and methods of the present invention rely on one or more glycosaminoglycans as a biological marker or an indicator of a biologic state (e.g., MPS) and may include a characteristic that is objectively measured as an indicator of normal biological processes, pathologic processes, or pharmacologic responses to a therapeutic or other intervention. In one particular embodiment of the present invention, the glycosaminoglycans are quantified indirectly. For example, the presence or quantity of a glycosaminoglycan may be assessed by analyzing such glycosaminoglycan's ability to catalyze a known enzymatic reaction. In one embodiment of the present invention, the glycosaminoglycans may be indicative of the presence of MPS or alternatively may be indicative of a MPS progression or regression (e.g., in response to the administration of a therapeutic agent.) In a preferred embodiment, the GAGs of the present invention comprise heparan sulfate (HS), dermatan sulfate (DS), chondroitin sulfate (CS), keratan sulfate (KS), hyaluronan and combinations thereof.

The methods and assays of the present invention are particularly sensitive and surprisingly retain such sensitivity irrespective of the selected biological sample. For example, the methods and assays of the present invention are capable of detecting low (e.g., on a nanogram scale) concentrations or quantities of one or more GAGs.

Figure 7:
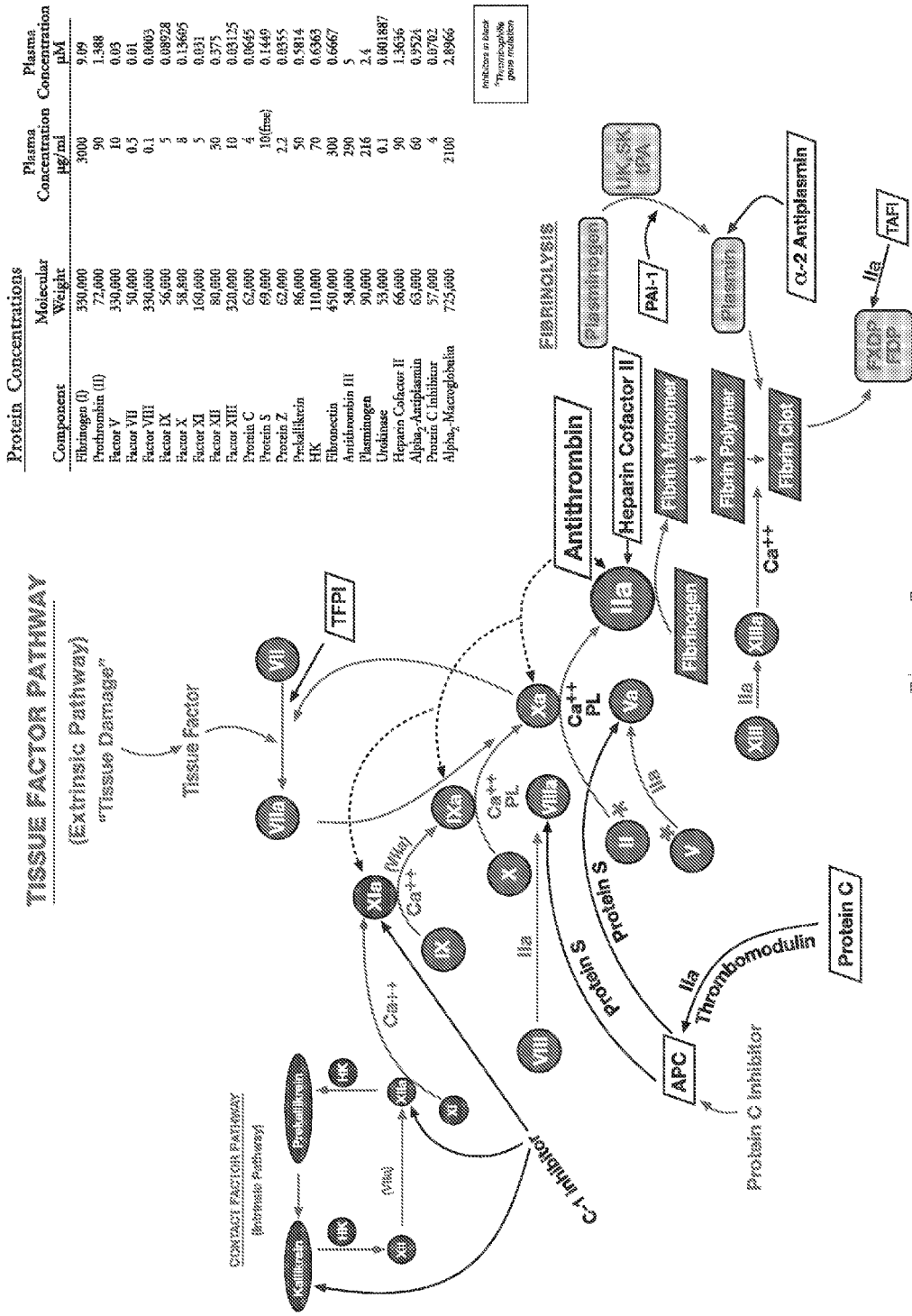
FIG. 7 illustrates the various enzymes and enzymatic actions involved in the proteolytic cascade of the coagulation pathway and shows serine proteases of the clotting (or complement) cascade.

The methods and assays of the present invention are based on the principle that inhibition of serine protease (SP) activity by a serine protease inhibitor (SERPIN) under optimal concentrations of the serine protease and the SERPIN is accelerated by the presence of GAGs (e.g., DS and/or HS). The assay reaction is depicted below,

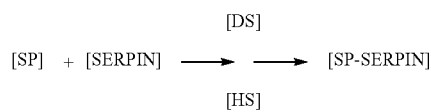

wherein DS is dermatan sulfate; HS is heparan sulfate; SP is active serine protease enzyme; SERPIN is serine protease inhibitor; and SP-SERPIN is the inactive serine protease/SERPIN-complex. It should be appreciated by those skilled in the art that any serine protease and any SERPIN involved in the proteolytic cascade of the coagulation pathway (e.g., blood clotting system) can be used in the assays and methods of the present invention. FIG. 7 illustrates the various enzymes SPs (e.g., Factor IXa, Xa, XIa and XIIa, etc.) and SERPINs (e.g., Antithrombin Ina, Heparin Cofactor II, etc.) and enzymatic actions involved in the proteolytic cascade of the coagulation pathway which is described in further detail below.

Figure 8:
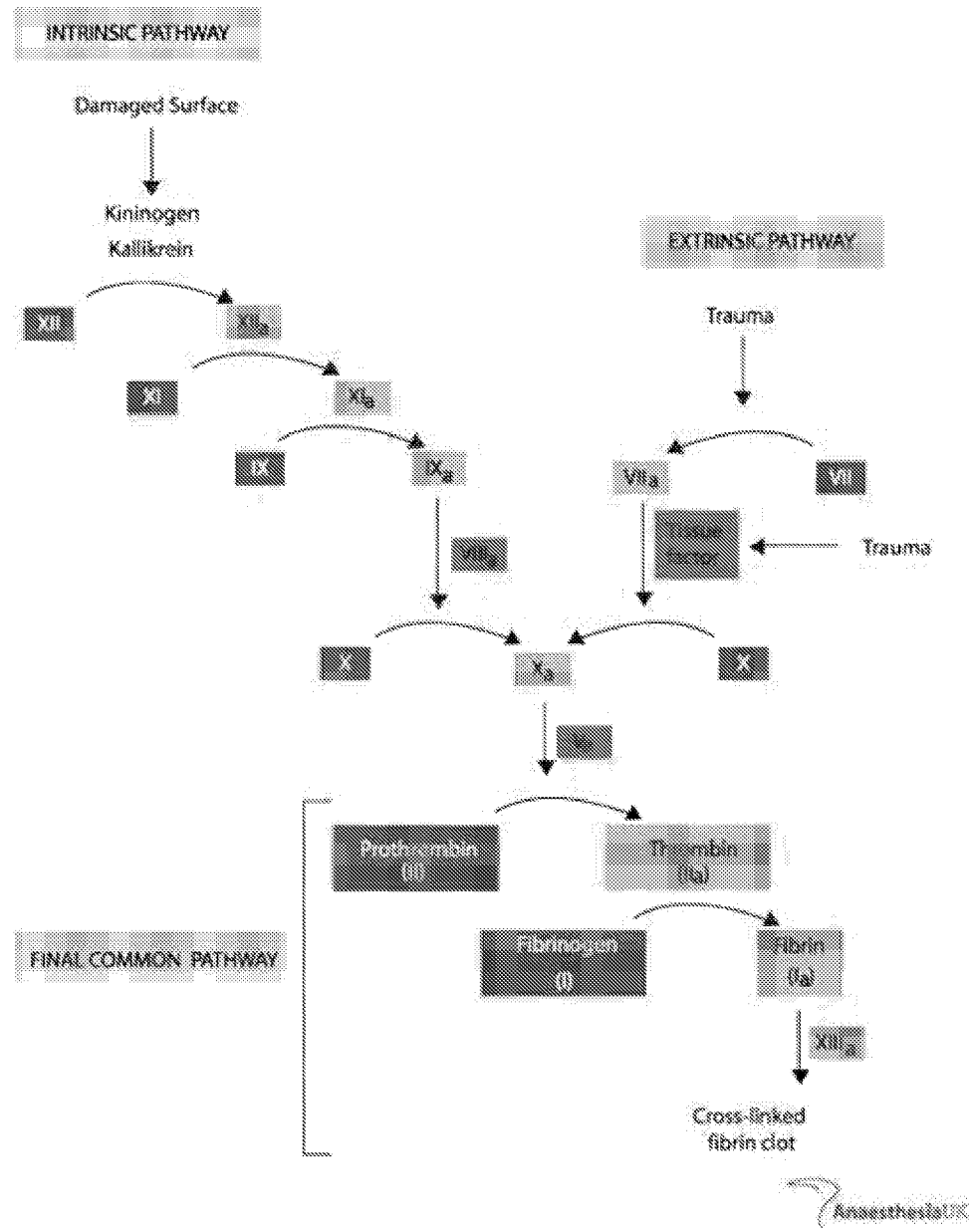
FIG. 8 illustrates how the generation of thrombin can be divided into three phases, the intrinsic and extrinsic pathways, which provide alternative routes for the generation of factor X, and the final common pathway, which results in thrombin formation.

The blood clotting system or coagulation pathway, like the complement system, is a proteolytic cascade. Each enzyme of the pathway is present in the plasma as a zymogen (inactive form), which on activation undergoes proteolytic cleavage to release the active factor from the precursor molecule. The coagulation pathway functions as a series of positive and negative feedback loops which control the activation process. The ultimate goal of the pathway is to produce thrombin, which can then convert soluble fibrinogen into fibrin, which forms a clot. As illustrated in FIG. 8, the generation of thrombin can be divided into three phases, the intrinsic and extrinsic pathways, which provide alternative routes for the generation of factor X, and the final common pathway, which results in thrombin formation.

The intrinsic pathway is activated when blood comes into contact with sub-endothelial connective tissues or with negatively charged surfaces that are exposed as a result of tissue damage. Quantitatively it is the more important of the two pathways, but is slower to cleave fibrin than the extrinsic pathway. The Hageman factor (factor XII), factor XI, prekallikrein and high molecular weight kininogen (HMWK) are involved in this pathway of activation. The first step is the binding of factor XII to a sub-endothelial surface exposed by an injury. A complex of prekallikrein and HMWK also interacts with the exposed surface in close proximity to the bound factor XII, which becomes activated. During activation, the single chain protein of the native factor XII is cleaved into two chains (50 and 28 kDa), which remain linked by a disulphide bond. The light chain (28 kDa) contains the active site and the molecule is referred to as activated Hageman factor (factor XIIa). There is evidence that the Hageman factor can autoactivate, thus the pathway is self-amplifying.

Activated factor XII, in turn, activates prekallikrein. The kallikrein produced can then also cleave factor XII, and a further amplification mechanism is triggered. The activated factor XII remains in close contact with the activating surface, such that it can activate factor XI, the next step in the intrinsic pathway, which, to proceed efficiently, requires calcium. Also involved at this stage is HMWK, which binds to factor XI and facilitates the activation process. Activated factors XIa, XIIa and kallikrein are all serine proteases.

The intrinsic pathway ultimately activates factor X, a process which can also be brought about by the extrinsic pathway. Factor X is the first molecule of the common pathway and is activated by a complex of molecules containing activated factor IX, factor VIII, calcium and phospholipid, which is provided by the platelet surface, where this reaction usually takes place. The precise role of factor VIII in this reaction is not clearly understood. Its presence in the complex is essential, as evidenced by the consequences of factor VIII deficiency experienced by haemophiliacs. Factor VIII is modified by thrombin, a reaction that results in greatly enhanced factor VIII activity, promoting the activation of factor X.

The extrinsic pathway is an alternative route for the activation of the clotting cascade. It provides a very rapid response to tissue injury, generating activated factor X almost instantaneously, compared with the seconds, or even minutes, required for the intrinsic pathway to activate factor X. The main function of the extrinsic pathway is to augment the activity of the intrinsic pathway.

There are two components unique to the extrinsic pathway, tissue factor or factor III, and factor VII. Tissue factor is present in most human cells bound to the cell membrane. Once activated, tissue factor binds rapidly to factor VII, which is then activated to form a complex of tissue factor, activated factor VII, calcium and a phospholipid, and this complex then rapidly activates factor X.

As shown in FIG. 8, the intrinsic and extrinsic systems converge at factor X to a single common pathway which is responsible for the production of thrombin (factor IIa). In certain embodiments, the methods and assays of the present invention are based on the principle that the inactivation of thrombin (T) by heparin cofactor-II (HC) under optimal concentrations of T and HC is accelerated by the presence of, e.g., DS and/or HS. Under these assay conditions, the concentration and/or quantity of DS and/or HS is the reaction rate limiting factor in the inhibition of T. The assay reaction is depicted below:

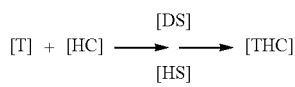

wherein DS is dermatan sulfate; HS is heparan sulfate; T is active thrombin enzyme; HC is thrombin inhibitor heparin cofactor II; and THC is the inactive thrombin/heparin cofactor II -complex.

Heparin cofactor-II (HC) belongs to a family of serine protease inhibitors (SERPINS) and its primary function is as an inhibitor of the enzyme thrombin (T). As used herein, the term "SERPIN" refers to serine protease inhibitors which are exemplified by species such as Heparin cofactor-II (HC). Heparin cofactor-II acts as an inhibitor of thrombin, and the inhibition of thrombin by heparin cofactor-II is accelerated by the presence of the GAGs DS and/or HS under conditions described herein.

Thrombin is a coagulation protein that affects the coagulation cascade and blood clotting. Thrombin is a serine protease and is responsible for converting soluble fibrinogen into insoluble strands of fibrin, as well as catalyzing many other coagulation-related reactions. The inhibition of thrombin by a SERPIN inhibitor results in an anticoagulant effect and this reaction is catalyzed by the GAGs DS, and to a lesser extent by HS. Thrombin is capable of cleaving thrombin substrates (e.g., a chromogenic thrombin substrate such as thrombin substrate S2238 which produces a chromogen with a measurable optical density at 405 nm). In accordance with the present invention, the inactivation of thrombin by heparin cofactor-II in the presence of DS and/or HS reduces the cleavage of the thrombin substrate. Accordingly, the methods and assays of the present invention provide means of quantifying the consumption of the chromogenic thrombin substrate (i.e., correlating to the inactivation of thrombin), for example using spectroscopy, and thus providing an indirect measurement of the concentration and/or quantity of DS and/or HS in the biological sample.

Figure 3:
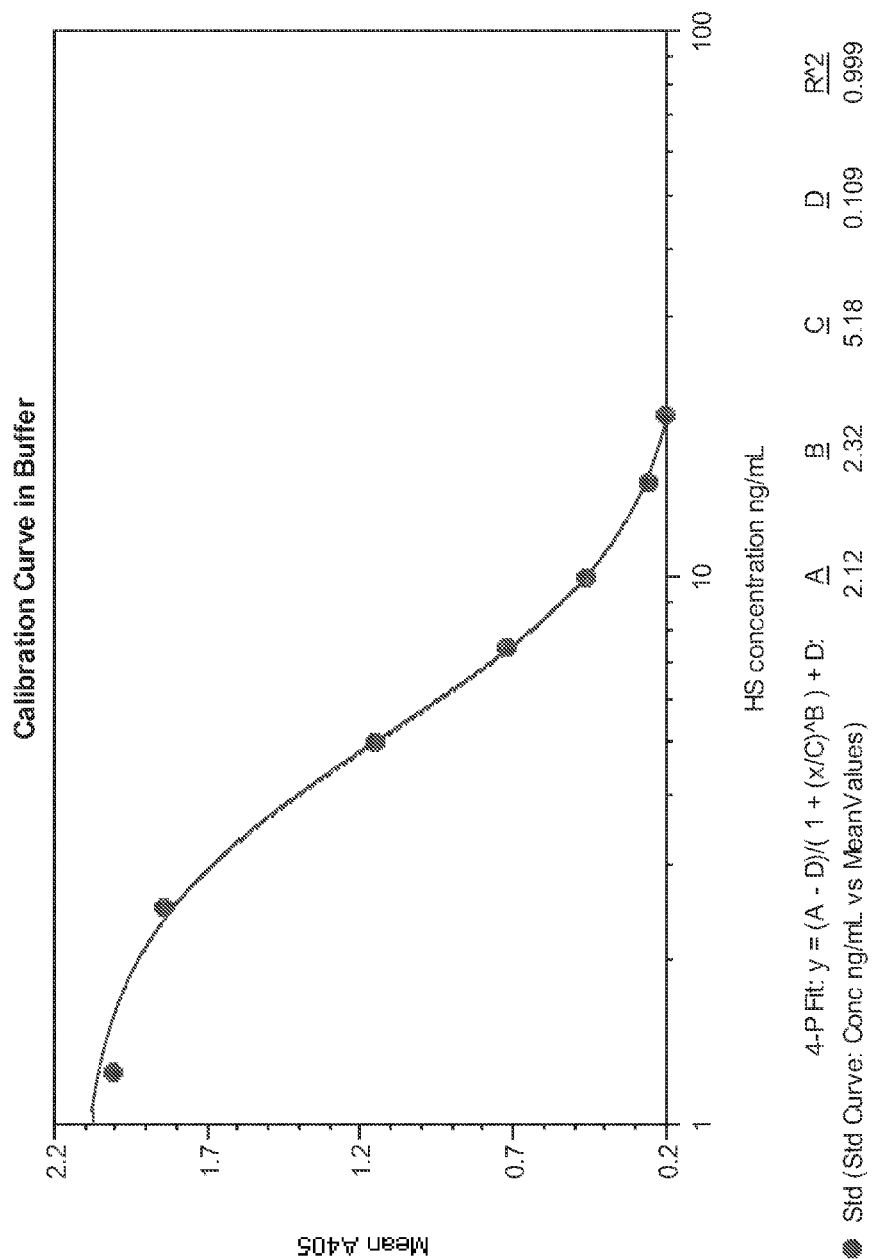
FIG. 3 illustrates sample Heparan Sulfate (HS) Standard Curve in Assay Buffer 2
Figure 5:
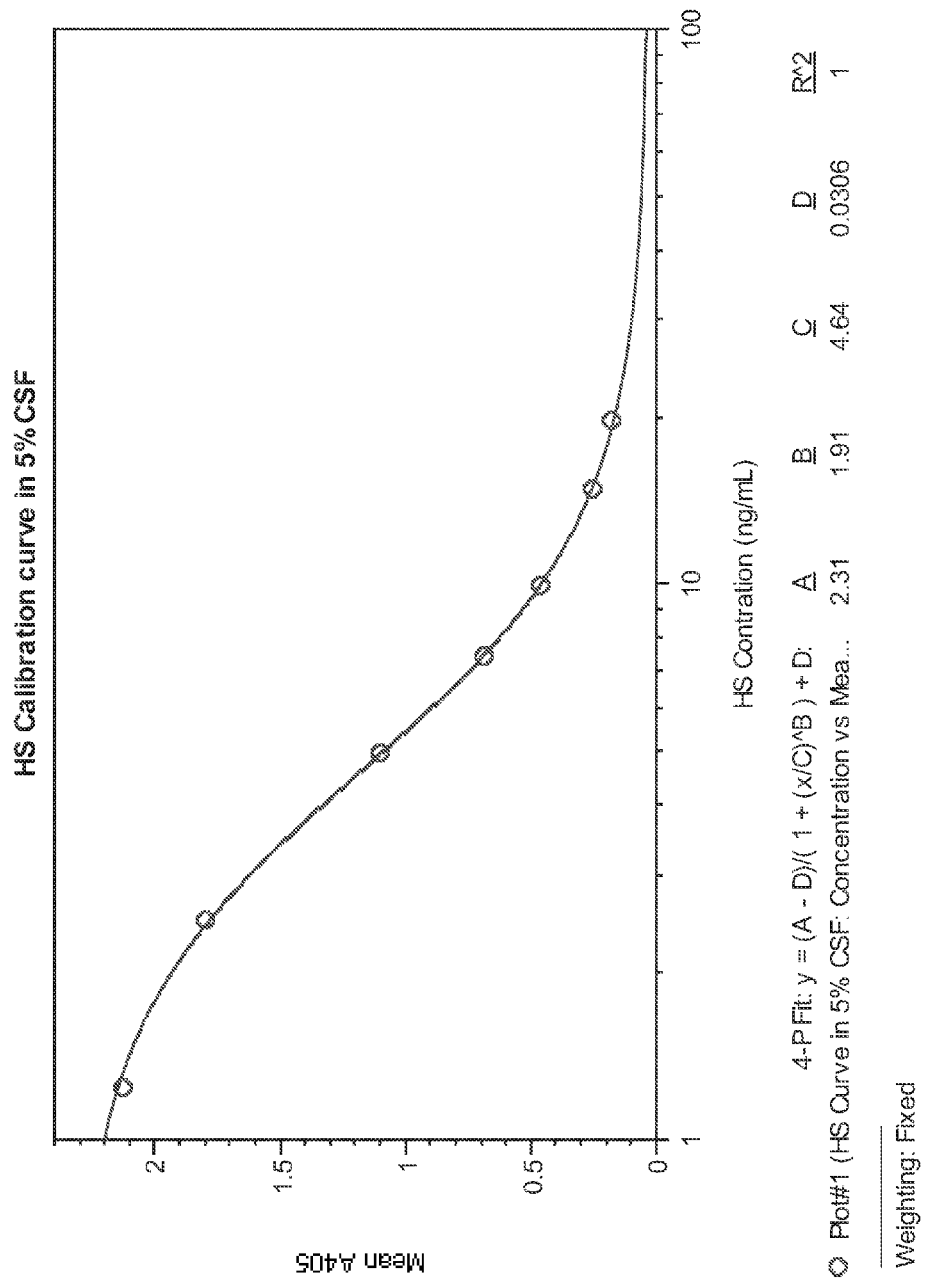
FIG. 5 illustrates sample Heparan Sulfate (HS) Standard Curve in 5% cerebrospinal fluid (CSF) in Assay Buffer 2.

In accordance with the present invention, as the DS/HS concentration increases in the biological sample, inhibition of thrombin increases and less thrombin substrate is cleaved by thrombin. The reduced cleavage of thrombin substrate by thrombin as a result of increasing DS/HS concentrations present in the biological sample is illustrated by decreasing absorbance measurements obtained by spectrophotometric detection at 405 nm, as shown in FIG. 1, FIG. 3, and FIG. 5. The absorbance of the chromogenic thrombin substrate may be determined and compared to a standard or calibration curve prepared by plotting the mean absorbance value for known standard solutions versus the corresponding concentrations of such standard solutions. As the phrase is used herein, a "calibration curve" refers to a graphical plot of two or more variables (e.g., known concentration of a GAG and optical density of a chromogen). Provided in FIGS. 1, 3 and 5 are calibration curves prepared using HS and DS standard solutions in accordance with the examples provided herein, providing the ability to comparatively assess the absorbance values of a biological sample and thereby quantify the DS and HS concentrations in that biological sample (e.g., urine or CSF). In one embodiment of the present invention, the calibration curves are preferably prepared using standards with known concentrations of one or more GAGs, such that the optical density of a sample may be readily correlated with the calibration curve and the concentration or quantity of GAG in such sample may be readily determined. Quantitative assessments of GAGs in a biological sample thereby provide a means of assessing MPS disease progression or treatment efficacy.

In some embodiments, the assays and methods of the present invention contemplate comparative analyses of the sample relative to one or more controls. For example, comparing a biological sample relative to a positive control (e.g., a biological sample obtained from a subject with MPS) may be indicative of the presence of MPS. Alternatively, a comparison of a biological sample with a negative control (e.g., a biological sample obtained from a subject without MPS) may be indicative of the absence of MPS. In another embodiment, the positive and negative controls may be used to construct a calibration or standards curve to which the sample may be compared to assess the presence or absence of MPS.

While certain methods, assays and kits of the present invention have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

EXAMPLES

The assays described in the following examples were conducted to assess the concentrations of total glycosaminoglycans and DS or HS in biological samples (e.g., urine and cerebrospinal fluid (CSF)) by using an exemplary serine protease-based assay as described herein. Spectrophotometric detection was performed using Molecular Devices SPECTRAmax plate reader with attached computer equipped with SOFTMax Pro software and assay template, however, any similar device suitable for performing spectrophotometric detection can be used in the methods, assays and kits of the present invention. Chemicals and Reagents used in the assays included: Thrombin Human Alpha (commercially available from Enzyme Research Catalog #HT 1002a); Human Heparin Cofactor 2 (commercially available from Haematologic Technologies Inc, Catalog #HCII-0190); Thrombin Substrate S-2238 (commercially available from Chromogenix-Diapharma Catalog #82-0324-39) reconstituted in purified water; Dermatan Sulfate from pig mucosa (commercially available from Iduron, Catalog #GAG-DS01); Heparan Sulfate sodiun salt, from bovine kidney, (commercially available from Sigma, Catalog #H7640-1MG, CAS: 57459-72-0); Recombinant Chondroitinase B (commercially available from Ibex Catalog #50-018, CAS:52227-83-5) diluted in Assay Buffer 1; Recombinant Heparinase I, II, III mixture (commercially available from Ibex, Catalog #50-010, CAS:9025-39-2 for Heparinase I, #50-011, CAS:na for Heparinase II and #50-012, CAS:37290-86-1 for Heparinase III) diluted in Assay Buffer 2; Polythylene Glycol 8000(P.E.G-8000) (commercially available from Fisher Catalog #BP233-100, CAS: 25322-68-3); HEPES (commercially available from Acros, Catalog #172571000, CAS:7365-45-9); Sodium Chloride (NaCl) (commercially available from Fisher catalog #S640-500, CAS:7647-14-5); Glacial Acetic Acid (commercially available from Fisher Catalog #A38-500 CAS:64-19-7); Purified water: Milli-Q or better grade; Assay Buffer 1 solution comprised of 10 mM Hepes, 50 mM NaCl and 0.25 mg/mL P.E.G-8000 at pH 7.5+0.05; Assay Buffer 2 solution comprised of 10 mM Hepes, 40 mM NaCl and 0.25 mg/mL P.E.G-8000 at pH 7.5+0.05; and a Stop Buffer comprised of 20% Acetic Acid in water.

The preparation of Positive and Negative Controls was as follows. The Positive DS Control Urine was obtained from a subject with MPS II and diluted in Assay Buffer 1. The Positive DS Control CSF was obtained from a subject with MPS II and diluted in Assay Buffer 1. The Positive HS Control Urine was obtained from a subject with MPS IIIa and diluted in Assay Buffer 2. The Positive HS Control CSF was obtained from a subject with MPS IIIa and diluted in Assay Buffer 2. The Negative DS Control Urine was obtained from a normal subject and diluted in Assay Buffer 1. The Negative DS Control CSF was obtained from a normal subject and diluted in Assay Buffer 1. The Negative HS Control Urine was obtained from a normal subject and diluted in Assay Buffer 2. The Negative HS Control CSF was obtained from a normal subject and diluted in Assay Buffer 2.

Example 1

The purpose of the following assay was to determine the concentration in a urine sample of total GAGs and dermatan sulfate (DS) by a thrombin-coupled method.

Urine unknown samples were diluted 1:100 in Assay Buffer 1 and treated at 37° C. for 2 hours with chondroitinase B (at a final concentration of 13 ng/mL) or left untreated, and incubated at 37° C. for 2 hours. It should be appreciated by those of ordinary skill in the art that dilution of the samples is not limited to 1:100, as such dilution is provided as an illustrative example. Following this incubation step, unknown urine samples, positive and negative DS urine controls and DS calibrator samples (serially diluted from 40 ng/mL to 2.5 ng/mL, i.e. 1 nM to 0.063 nM, in Assay Buffer 1) were incubated with heparin cofactor II (at a final concentration of 4.68 µg/mL i.e. 71.4 nM) at 37° C. for 5 minutes. Human thrombin was added to all tubes at a final concentration of 0.15 µg/mL i.e. 4 nM and all tubes were incubated at 37° C. for an additional 15 minutes. Thrombin substrate was then added to all tubes at a final concentration of 0.5 mM and incubated at 37° C. for 30 minutes. The reaction was stopped by adding Stop solution. The signal was then read on a plate reader at a wavelength of 405 nm.

The absorbance value for each sample was then correlated to the dermatan sulfate calibrator curve (as in the example shown in FIG. 1) and the results reported as ng/mL of GAGs in each sample (as in the example shown in FIG. 2). For each unknown sample, the concentration of total GAGs is the value obtained from the sample left untreated by chondroitinase B (Table 2). The concentration of DS is the value obtained from subtracting the value obtained from the sample treated by chondroitinase B from the total GAGs value (Table 3).

Example 2

The purpose of the following assay was to determine the concentration in a cerebrospinal fluid (CSF) sample of total Glycosaminoglycans (GAGs) and dermatan sulfate (DS) by a thrombin-coupled method.

CSF unknown samples were diluted 1:5 in Assay Buffer 1 and treated at 37° C. for 2 hours with chondroitinase B (at a final concentration of 13 ng/mL) or left untreated, and incubated at 37° C. for 2 hours. It should be appreciated by those of ordinary skill in the art that dilution of the samples is not limited to 1:5, as such dilution is provided as an illustrative example. Following this incubation step, unknown CSF samples, positive and negative DS CSF controls and DS calibrator samples (serially diluted from 40 ng/nL to 2.5 ng/mL, i.e. 1 nM to 0.063 nM, in Assay Buffer 1) were incubated with heparin cofactor II (at a final concentration of 4.68 μg/mL, i.e. 71.4 nM) at 37° C. for 5 minutes. Human thrombin was added to all tubes at a final concentration of 0.15 μg/mL (i.e. 4 nM) and all tubes were incubated at 37° C. for an additional 15 minutes. Thrombin substrate was then added to all tubes at a final concentration of 0.5 mM and incubated at 37° C. for 30 minutes. The reaction was stopped by adding Stop solution. The signal was then read on a plate reader at a wavelength of 405 nm.

The absorbance value for each sample was then correlated to the dermatan sulfate calibrator curve (as in the example shown in FIG. 1) and the results reported as ng/mL, of GAGs in each sample (as in the example shown in FIG. 2). For each unknown sample, the concentration of total GAGs is the value obtained from the sample left untreated by chondroitinase B (Table 2). The concentration of DS is the value obtained from subtracting the value obtained from the sample treated by chondroitinase B from the total GAGs value (Table 3).

TABLE 2

Sample absorbance values for total GAGs
and GAGs after Chondroitinase B treatment

| Sample Type | Sample No. | Dilution | Absorbance at 405 nm | |
|---|---|---|---|---|
| | | | Total GAG | Chondroitinase B |
| CSF | A | 10 | 0.720 | 2.078 |
| CSF | B | 15 | 0.333 | 2.197 |
| CSF | C | 20 | 0.490 | 2.197 |
| CSF | D | 20 | 0.495 | 2.198 |
| Urine | E | 400 | 0.425 | 2.025 |
| Urine | F | 200 | 0.441 | 2.137 |
| Urine | G | 800 | 0.292 | 2.233 |

TABLE 3

Sample GAG concentration values for total GAGs, GAGs after
Chondroitinase B treatment, and final DS values.

| Sample Type | Sample No. | Dilution | Concentration (ng/mL) | | |
|---|---|---|---|---|---|
| | | | Total GAG | Chondroitinase B | DS |
| CSF | A | 10 | 259.10 | 49.30 | 209.80 |
| CSF | B | 15 | 316.85 | ND | 316.85 |
| CSF | C | 20 | 332.40 | ND | 332.40 |
| CSF | D | 20 | 331.00 | ND | 331 |
| Urine | E | 400 | 7144 | 1640 | 5504 |
| Urine | F | 200 | 3704 | 876 | 2828 |
| Urine | G | 800 | 18072 | 2280 | 15792 |

ND: Not Detectable

Example 3

The purpose of the following assay was to determine the concentration in a urine sample of total GAGs and heparan sulfate (HS) by a thrombin-coupled method.

Urine unknown samples were diluted 1:100 in Assay Buffer 2 and treated at 37° C. for 2 hours with heparinase I, II, and III mixture (at a final concentration of 180 ng/mL) or left untreated, and incubated at 37° C. for 2 hours. It should be appreciated by those of ordinary skill in the art that dilution of the samples is not limited to 1:100, as such dilution is provided as an illustrative example. Following this incubation step, unknown urine samples, positive and negative HS urine controls and HS calibrator samples (serially diluted from 20 ng/nL to 1.25 ng/mL, i.e. 0.5 nM to 0.03 nM, in Assay Buffer 2) were incubated with heparin cofactor II (at a final concentration of 4.68 μg/mL i.e. 71.4 nM) at 37° C. for 5 minutes. Human thrombin was added to all tubes at a final concentration of 0.15 μg/mL i.e. 4 nM and all tubes were incubated at 37° C. for an additional 15 minutes. Thrombin substrate was then added to all tubes at a final concentration of 0.5 mM and incubated at 37° C. for 30 minutes. The reaction was stopped by adding Stop solution. The signal was then read on a plate reader at a wavelength of 405 nm.

The absorbance value for each sample was then correlated to the heparan sulfate calibrator curve (as in the example shown in FIG. 3) and the results reported as ng/mL of GAGs in each sample (as in the example shown in FIG. 4). For each unknown sample, the concentration of total GAGs is the value obtained from the sample left untreated by the heparinase mixture (Table 4). The concentration of HS is the value obtained from subtracting the value obtained from the sample treated by the heparinase mixture from the total GAGs value (Table 5).

Example 4

The purpose of the following assay was to determine the concentration of total GAGs and heparan sulfate (HS) in a CSF sample by a thrombin-coupled method.

CSF samples were diluted 1:20 in Assay Buffer 2 and treated at 37° C. for 2 hours with a heparinase I, II, and III mixture (at a final concentration of 180 ng/mL)) or left untreated and incubated at 37° C. for 2 hours. It should be appreciated by those of ordinary skill in the art that dilution of the samples is not limited to 1:20, as such dilution is provided as an illustrative example. Following this incubation step, unknown CSF samples, positive and negative HS CSF controls and HS calibrator samples (serially diluted from 20 ng/nL to 1.25 ng/mL, i.e. 0.5 nM to 0.03 nM, in 1:20 normal pooled human CSF in Assay Buffer 2) were incubated with heparin cofactor II (at a final concentration of 4.68 μg/mL i.e. 71.4 nM) at 37° C. for 5 minutes. Human thrombin was added to all tubes at a final concentration of 0.15 μg/mL (i.e. 4 nM) and all tubes were incubated at 37° C. for an additional 15 minutes. Thrombin substrate was then added to all tubes at a final concentration of 0.5 mM and incubated at 37° C. for 30 minutes. The reaction was stopped by adding Stop solution. The signal was then read on a plate reader at a wavelength of 405 nm.

The absorbance value for each sample was then correlated to the heparan sulfate calibrator curve (as in the example shown in FIG. 5) and the results reported as ng/mL of GAGs in each sample (as shown in the example shown in FIG. 6). For each unknown sample, the concentration of total GAGs is the value obtained from the sample left untreated by the heparinase mixture (Table 4). The concentration of HS is the value obtained from subtracting the value obtained from the sample treated by the heparinase mixture from the total GAGs value (Table 5).

TABLE 4

Sample GAG absorbance values for total GAGs,
GAGs after Heparinase mixture treatment.

| Sample Type | Sample No. | Dilution | Absorbance at 405 nm | |
|---|---|---|---|---|
| | | | Total GAG | Heparinase Mixture |
| CSF | A | 20 | 0.923 | 2.018 |
| CSF | B | 20 | 0.749 | 1.930 |

TABLE 4-continued

Sample GAG absorbance values for total GAGs,
GAGs after Heparinase mixture treatment.

| | | | Absorbance at 405 nm | |
|---|---|---|---|---|
| Sample Type | Sample No. | Dilution | Total GAG | Heparinase Mixture |
| CSF | C | 20 | 0.798 | 1.969 |
| CSF | D | 20 | 0.648 | 1.786 |
| Urine | E | 800 | 0.548 | 2.069 |
| Urine | F | 3200 | 0.462 | 2.072 |
| Urine | G | 3200 | 0.686 | 2.130 |

TABLE 5

Sample GAG concentration values for total GAGs, GAGs after
Heparinase mixture treatment, and final HS values.

| | | | Concentration (ng/ml) | | |
|---|---|---|---|---|---|
| Sample Type | Sample No. | Dilution | Total GAG | Heparinase Mixture | HS |
| CSF | A | 20 | 144.10 | ND | 144.10 |
| CSF | B | 20 | 173.80 | 35.0 | 138.80 |
| CSF | C | 20 | 132.20 | ND | 132.20 |
| CSF | D | 20 | 158.10 | 38.9 | 119.20 |
| Urine | E | 800 | 7466.32 | ND | 7466.32 |
| Urine | F | 3200 | 33949.82 | ND | 33949.82 |
| Urine | G | 3200 | 25334.60 | ND | 25334.60 |

ND: Not Detectable

What is claimed is:

1. A method for determining the concentration of one or both of dermatan sulfate (DS) and heparin sulfate (HS) in a sample, the method comprising (a) treating a sample with at least one of chondroitinase B and one or more heparineses, (b) combining a serine protease shown in FIG. 7 or 8 a labeled substrate for said serine protease, an inhibitor of said serine protease, and the sample under conditions and for a time suitable for cleavage of the labeled substrate by the serine protease to produce a detectable signal, (c) detecting the detectable signal, and (d) comparing the amount of detectable signal with a standard to determine the concentration of said one or both of DS and HS in said sample.

2. The method according to claim 1, wherein the labeled substrate is a chromogenic or fluorogenic substrate.

3. The method according to claim 1, wherein the serine protease is thrombin and the labeled substrate is a chromogenic thrombin substrate.

4. The method according to claim 1, wherein detecting the detectable signal is performed by spectrophotometric detection.

5. The method according to claim 1, wherein the standard is a curve which calibrates spectrophotometric absorbance with glycosaminoglycan concentration.

6. The method of claim 1, wherein said inhibitor of said serine protease is selected from the group consisting of heparin cofactor II and antithrombin III.

7. A method for determining the concentration of one or both of dermatan sulfate (DS) and heparan sulfate (HS) in a sample, the method comprising (a) combining a serine protease shown in FIG. 7 or FIG. 8, a labeled substrate for said serine protease, an inhibitor of said serine protease, and a cerebrospinal fluid sample under conditions and for a time suitable for cleavage of the labeled substrate by the serine protease to produce a detectable signal, (b) detecting the detectable signal, and (c) comparing the amount of detectable signal with a standard to determine the concentration of said one or both of DS and HS in said sample.

8. The method of claim 7, wherein the labeled substrate is a chromogenic or fluorogenic substrate.

9. The method of claim 7, wherein the serine protease is thrombin and the labeled substrate is a chromogenic thrombin substrate.

10. The method of claim 7, wherein detected the detectable signal is performed by spectrophotometric detection.

11. The method of claim 7, wherein the standard is a curve which calibrates spectrophotometric absorbance with glycosaminoglycan concentration.

12. The method of claim 7, wherein said inhibitor of said serine protease is selected from the group consisting of heparin cofactor II and antithrombin III.

13. The method of claim 7, wherein the sample is treated with at least one of chondroitinase B and one or more heparinases.

* * * * *